(12) United States Patent
Fong et al.

(10) Patent No.: US 8,115,039 B2
(45) Date of Patent: Feb. 14, 2012

(54) CATALYTIC DISTILLATION PROCESS FOR PRIMARY HALOALKANES

(75) Inventors: Howard Lam-Ho Fong, Sugar Land, TX (US); Brendan Dermot Murray, Houston, TX (US); Thomas Carl Semple, Friendswood, TX (US)

(73) Assignee: Shell Oil Company, Houston, TX (US)

( * ) Notice: Subject to any disclaimer, the term of this patent is extended or adjusted under 35 U.S.C. 154(b) by 928 days.

(21) Appl. No.: 11/887,195

(22) PCT Filed: Mar. 24, 2006

(86) PCT No.: PCT/US2006/010848
§ 371 (c)(1),
(2), (4) Date: Sep. 26, 2007

(87) PCT Pub. No.: WO2006/104909
PCT Pub. Date: Oct. 5, 2006

(65) Prior Publication Data
US 2009/0032437 A1    Feb. 5, 2009

Related U.S. Application Data

(60) Provisional application No. 60/665,663, filed on Mar. 28, 2005.

(51) Int. Cl.
*C07C 21/00* (2006.01)
(52) U.S. Cl. ..................................................... 570/256
(58) Field of Classification Search .................. None
See application file for complete search history.

(56) References Cited

U.S. PATENT DOCUMENTS

| | | | |
|---|---|---|---|
| 2,393,509 A | 5/1941 | Archibald et al. | 204/163 |
| 2,302,121 A | 11/1942 | Harris | 260/615 |
| 2,716,140 A | 8/1955 | McBee et al. | 260/648 |
| 3,326,758 A | 6/1967 | Irmscher et al. | 167/65 |
| 3,341,615 A | 9/1967 | Wulf et al. | 260/677 |
| 3,401,206 A | 9/1968 | Wulf et al. | 260/666 |
| 3,644,547 A | 2/1972 | Schmerling | 260/658 |
| 3,664,961 A | 5/1972 | Norris | 252/99 |
| 3,786,112 A | 1/1974 | Reusser et al. | 260/683 |
| 3,919,143 A | 11/1975 | Morris | 260/18 R |
| 3,959,391 A | 5/1976 | Allain | 260/615 B |
| 4,016,245 A | 4/1977 | Plank et al. | 423/328 |
| 4,076,842 A | 2/1978 | Plank et al. | 423/328 |
| 4,251,499 A | 2/1981 | Nanne et al. | 423/329 |
| 4,556,477 A | 12/1985 | Dwyer | 208/111 |
| 4,706,749 A | 11/1987 | Hayes et al. | 166/267 |
| 4,727,203 A | 2/1988 | Hamilton, Jr. | 585/329 |
| 4,749,819 A | 6/1988 | Hamilton, Jr. | 585/329 |
| 5,177,281 A | 1/1993 | Haag et al. | 585/324 |
| 5,276,226 A * | 1/1994 | Horvath et al. | 570/253 |
| 5,427,711 A | 6/1995 | Sakaguchi et al. | 252/174.25 |
| 5,985,238 A | 11/1999 | Pasquale et al. | 423/706 |
| 6,017,875 A | 1/2000 | Kadono et al. | 510/506 |
| 6,291,719 B1 | 9/2001 | Gao et al. | 568/596 |
| 6,462,243 B1 | 10/2002 | Zhou et al. | 568/893 |
| 6,465,696 B1 | 10/2002 | Zhou et al. | 568/671 |
| 6,465,699 B1 | 10/2002 | Grosso | 568/893 |
| 6,472,572 B1 | 10/2002 | Zhou et al. | 568/893 |
| 6,486,368 B1 | 11/2002 | Zhou et al. | 568/893 |
| 7,091,387 B2 * | 8/2006 | Fong et al. | 568/893 |
| 2003/0220187 A1 * | 11/2003 | Yang et al. | 502/60 |
| 2004/0177958 A1 | 9/2004 | Shpakoff et al. | 166/270.1 |
| 2005/0048091 A1 | 3/2005 | Raney et al. | 424/401 |
| 2005/0153869 A1 | 7/2005 | Condor et al. | 510/515 |
| 2005/0196362 A1 | 9/2005 | Carty et al. | 424/59 |
| 2005/0245777 A1 | 11/2005 | Fong et al. | 585/324 |

FOREIGN PATENT DOCUMENTS

| | | |
|---|---|---|
| DE | 330642 | 12/1920 |
| DE | 436999 | 11/1926 |
| DE | 746888 | 6/1944 |
| GB | 705734 | 3/1954 |
| WO | WO9959947 | 11/1999 |
| WO | WO2005105715 | 11/2005 |
| WO | WO2006104883 | 10/2006 |
| WO | WO2006104909 | 10/2006 |

OTHER PUBLICATIONS

Sulzbaher, et al: "Dialkylthers of Ethyleneglycol and Diethylene Glycol", J. Am. Chem. Soc, vol. 72, 1950, pp. 2795-2796.
Riemschneider, et al: "Konstitution and Physikalsiche Eigenschaften von Athern, 3. Mitt., Monatsh. Chem.", vol. 90, 1959, pp. 783-786.
Kemp, Daniel:"Advanced Inorganic Chemistry, 4$^{th}$ Edition", Worth Publishers, 1980, pp. 94-95.

* cited by examiner

*Primary Examiner* — Sudhakar Katakam

(57) ABSTRACT

A process for making primary haloalkanes by catalytic distillation of internal haloalkanes which comprises a) introducing an internal haloalkane feed into a catalytic distillation column; b) isomerizing at least a portion of the internal haloalkane feed in the presence of an internal haloalkane isomerization catalyst at a temperature at or above the boiling point of the internal haloalkanes and below the temperature and pressure at which hydrogen halide is formed to form primary haloalkanes; and removing the primary haloalkanes from the catalytic distillation column.

18 Claims, 1 Drawing Sheet

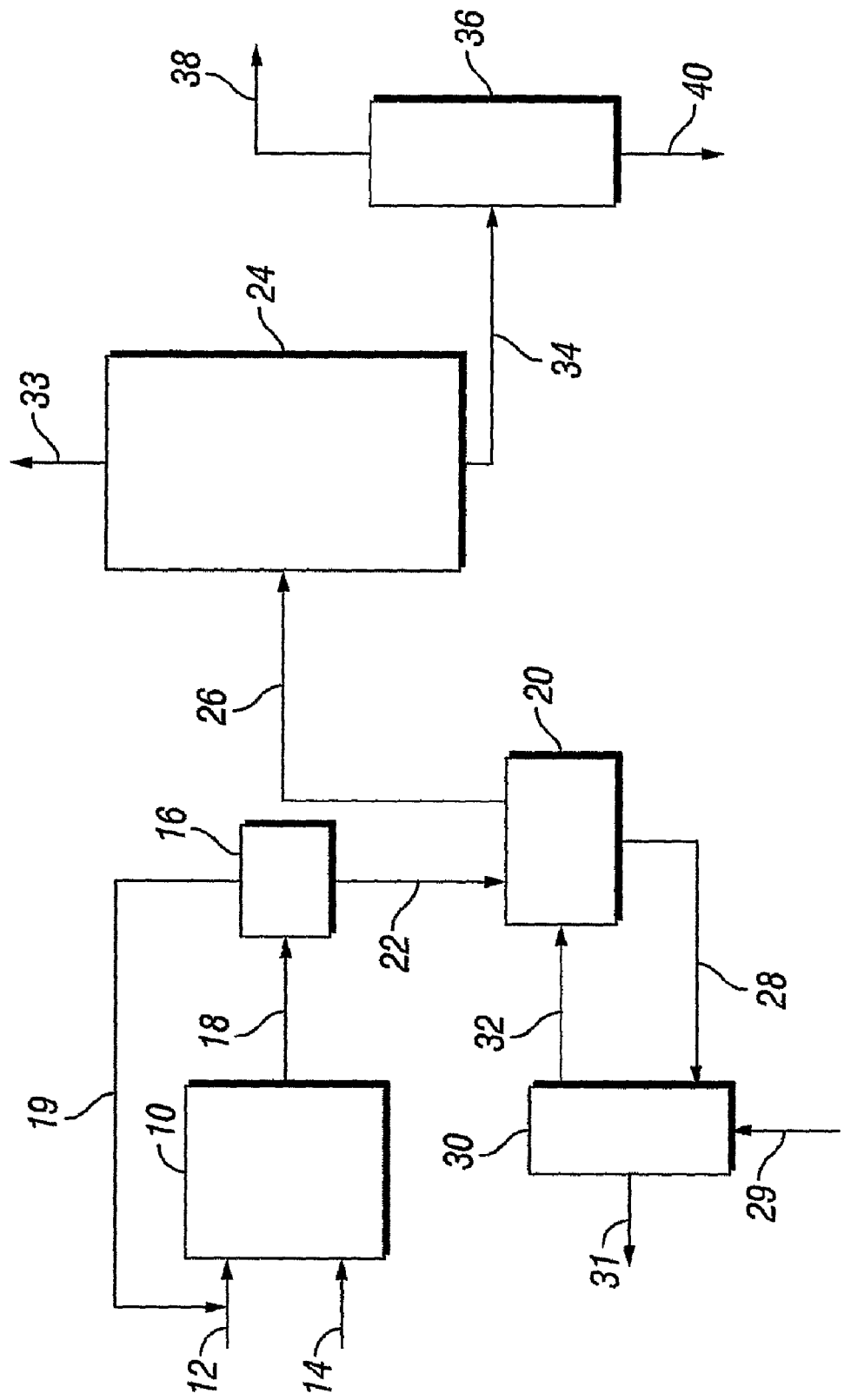

CATALYTIC DISTILLATION PROCESS FOR PRIMARY HALOALKANES

The present application claims priority from U.S. Provisional Patent Application No. 60/665,663 filed 28 Mar. 2005.

FIELD OF THE INVENTION

This invention relates to a method for producing primary haloalkanes from internal haloalkanes. More particularly, this invention relates to a process for making primary haloalkanes by catalytic distillation of internal haloalkanes.

BACKGROUND OF THE INVENTION

It has long been known that primary haloalkanes (sometimes referred to as halogenated alkanes) could be very useful in many chemical reactions to add alkyl groups to another material (paraffin activation). However, longer chain primary haloalkanes have proven to be enormously difficult and/or expensive to manufacture in significant commercial quantities. Internal haloalkanes are highly thermodynamically preferred and efforts to isolate primary haloalkanes have resulted in low yields and high cost.

The current problem in paraffin activation is the inability to produce an alkane activated in the primary position in a thermal and/or catalytic and selective way that yields product with a useable rate of reaction. Current routes suffer from restrictive rates and the lack of selectivity (air oxidation). Some routes are stoichiometric in an expensive reactant (i.e., boron) and some use difficult to make "pincer" ligands with rhodium.

SUMMARY OF THE INVENTION

This invention provides an improved way to produce primary haloalkanes (PHA). The invention provides a catalytic distillation method for starting with the kinetically favored internal haloalkanes and make the thermodynamic distribution of haloalkane isomers while separating out the desired PHAs. A process for making primary monohaloalkanes by catalytic distillation of internal haloalkanes may comprise:
   a) introducing an internal haloalkane feed into a catalytic distillation column;
   b) isomerizing at least a portion of the internal haloalkane feed in the presence of an internal haloalkane isomerization catalyst at a temperature at or above the boiling point of the internal haloalkane and below the temperature and pressure at which hydrogen halide is formed to form PHAs; and
   c) removing the PHAs from the catalytic distillation column.

The present invention also provides a process for making primary haloalkanes from alkanes. This process may comprise:
   a) halogenating at least one alkane to produce at least one internal haloalkane;
   b) introducing the internal haloalkane into a catalytic distillation column;
   c) isomerizing at least a portion of the internal haloalkane in the presence of an internal haloalkane isomerization catalyst at a temperature at or above the boiling point of the internal haloalkane and below the temperature and pressure at which hydrogen halide is formed to form at least one primary haloalkane; and
   d) removing the primary haloalkane from the catalytic distillation column.

The halogenation step may also form other haloalkanes including internal dihaloalkanes, internal haloalkanes having 3 or more halogens, and possibly some primary haloalkanes. In another embodiment, this invention provides a process for separating the monohaloalkanes from the haloalkanes which contain 2 or more halogens, preferably by distillation, and then hydrogenating the haloalkanes which contain 2 or more halogens under similar conditions as the hydrogenation of olefins to paraffins to produce primary and/or internal monohaloalkanes which may be recycled to the monohaloalkane separation step.

Other embodiments include methods for enhanced oil recovery, making detergents, and making personal care compositions from haloalkanes and/or paraffins.

BRIEF DESCRIPTION OF THE DRAWING

FIG. 1 is a block flow diagram for the production of primary haloalkanes from their corresponding alkanes.

DETAILED DESCRIPTION OF THE INVENTION

The haloalkanes for use herein may be made by any process suitable for making haloalkanes. One method is by halogenation of alkanes as described in U.S. Pat. Nos. 6,462,243, 6,465,699, 6,472,572, 6,486,368, and 6,465,696, all of which are herein incorporated by reference in their entirety, and in copending U.S. application Ser. No. 60/563,966, filed Apr. 21, 2004, entitled "Process to Convert Linear Paraffins into Alpha Olefins", published on Nov. 3, 2005 as U.S. published patent application 2005/0245777, the entire disclosure of which is herein incorporated by reference. Another method of making haloalkanes is the Wohl-Ziegler bromination of hydrocarbons with N-bromosuccinimide. The haloalkanes for use in the coupling reaction may include mono- and dihaloalkanes as well as haloalkanes containing more than 2 halogens. Alkanes of particular interest as the starting material are linear alkanes, branched alkanes, or combinations of linear alkanes and/or branched alkanes.

The reaction products of the halogenation may include internal haloalkanes, unreacted alkane, and hydrogen halide. These materials may be separated, for example, by distillation, from the haloalkanes and the unreacted alkane may preferably be recycled.

The internal haloalkanes likely contain mono- and dihaloalkanes and may contain some haloalkanes with more than 2 halogens. It is important that the monohaloalkanes be separated from the other materials. This may be accomplished by distillation or other methods.

The heavier stream will contain the dihaloalkanes and the haloalkanes with more than 2 halogens. This stream may be subjected to partial hydrogenation to convert it to monoalkanes which can be recycled to the monohaloalkane separation step. This option is exemplified in Example 2 below. Hydrogen halide may be a byproduct which could be treated to regenerate the halogen. Alternatively, the heavier stream may be completely hydrogenated to produce alkane and halogen which may be recycled.

The hydrogenation may take place in the presence of a hydrogenation catalyst. Substantially any of the known heterogeneous or homogeneous hydrogenation catalysts may be used. Useful hydrogenation catalysts include any of those based upon Group VIII metals, including nickel, cobalt, ruthenium, platinum and palladium, as well as copper, zinc and chromium and mixtures and alloys thereof. Suitable hydrogenation catalysts comprise a metal having an atomic number of from 26 to 78, which includes but is not necessarily limited to Fe, Co, Ni, Cu, Zn, Ga, Ge, As, Se, Br, Kr, Rb, Sr, Y, Zr, Nb, Mo, Tc, Ru, Rh, Pd, Ag, Cd, In, Sn, Sb, Te, I, Xe, Cs, Ba, the lanthanide series (comprising Ce, Pr, Nd, Pm, Sm, Eu, Gd, Th, Dy, No, Er, Tm, Yb, Lu), Hf, Ta, W, Re, Os, Ir, Pt. Preferred metals for the hydrogenation catalyst have an atomic number of 28 to 78 [Ni, Cu, Zn, Ga, Ge, As, Se, Br, Kr, Rb, Sr, Y, Zr, Nb, Mo, Tc, Ru, Rh, Pd, Ag, Cd, In, Sn, Sb, Te, I, Xe, Cs, Ba, the lanthanide series (comprising Ce, Pr, Nd, Pm, Sm, Eu, Gd, Th, Dy, No, Er, Tm, Yb, Lu), Hf, Ta, W, Re, Os, Ir, Pt]. Other known catalysts suitable for hydrogenation include the oxides and sulfides of Group VI, including but not necessarily limited to Cr, Mo and W. Hydrogenation is generally carried out at an elevated temperature during at least a portion of the hydrogenation step, generally within the range of 50° C. to 1000° C., under a hydrogen pressure of at least 100 psig to 5000 psig, generally within the range of 200 to 2000 psig.

The catalytic distillation may be carried out in a catalytic distillation column. Generally, the feed will have no primary haloalkane or only a very small amount. The thermodynamic equilibrium for monobromooctanes, for example, yields about 6 mole % primary monobromooctane, about 30 mole % of the 2-monobromooctane, about 32 mole % of the 3-monobromooctane, and about 32 mole % of the 4-monobromooctane at 180° C.

The thermodynamic equilibrium described above is established by the isomerization reaction which takes place in the catalytic distillation column. The primarily internal monohaloalkanes are isomerized to form the primary monohaloalkanes which are taken out of the column as the bottoms stream. This bottoms stream may contain some heavy dimers which may be removed by distillation. The light ends from the catalytic distillation column may contain hydrogen halide, internal olefins, and some cracked products. The internal monohaloalkanes remain in the column for further reaction.

Normal isomerization conditions may be range from 150° C. to 500° C. and pressure ranging from 0.1 atmospheres (10 kPa) to 20 atmospheres (2026 kPa). The isomerization reaction conditions herein are constrained in that a simultaneous distillation process is taking place in the column. The temperature must be at or above the boiling point of the internal haloalkanes (generally, the boiling points of these internal haloalkanes are very close). High temperatures may be used if desired but if the temperature is too high, hydrogen halide will form and product will be lost. It is preferred that the temperature in the column be below the temperature at which hydrogen halide is lost but it may be acceptable to operate at a temperature 400° C. above the hydrogen halide formation temperature because using a closed system would increase the pressure and allow the hydrogen halide to add back to any olefin that formed. For example, the catalytic distillation of monobromooctane may preferably be carried out from 188° C., the boiling point of the internal monobromooctanes, to 201° C., the temperature at which the HBr eliminates from the monobromooctane compound at atmospheric pressure.

Any isomerization catalyst may be used in the catalytic distillation column. Zeolites may be used as well as noble metal catalysts on supports. For example, plantinum, palladium, bismuth, tin, and combinations thereof can be used on MgO, $SiO_2$, $Al_2O_3$, and carbon supports.

Catalysts that may be used include alumino silicate ferrierite catalysts such as the ZSM-35 alumino silicate described in U.S. Pat. No. 4,016,245, the disclosure of which is incorporated herein by reference in its entirety, or by a piperidine derived ferrierite as described in U.S. Pat. Nos. 4,251,499 and 5,985,238, the disclosures of which are herein incorporated by reference in their entirety. Other zeolites of sufficient channel size include Theta-1, ZSM-12, ZSM-22, ZSM-23, and ZSM-48. The ZSM-22 catalyst is more particularly described in U.S. Pat. No. 4,556,477, the entire contents of which are herein incorporated by reference. The ZSM-23 catalyst is more particularly described in U.S. Pat. No. 4,076,842, the entire contents of which are herein incorporated by reference. The zeolites may be impregnated, co-mulled or ion exchanged using known methods to incorporate metal(s) and metal ions such as those listed earlier in this document.

Among the isomerization catalysts that can be used are the catalysts which are disclosed in U.S. Pat. Nos. 3,786,112, 4,749,819, 4,727,203, and 5,177,281, which are herein incorporated by reference.

The catalysts described below for the homogenous catalyst system for the reaction with the nucleophilic materials may also be used in the isomerization reaction. A partial list of these catalysts includes zinc bromide, $CoBr_2$, copper bromide, nickel bromide, copper chloride, iron bromide, zinc oxide, magnesium oxide, iron oxide, ZnO/FeO, palladium on a carbon support, and Fe on MgO.

The primary haloalkanes may be converted into useful products such as by reaction with a metal oxide or metal oxides to produce internal olefins, alcohols, olefin oxides, ether, and aldehydes. Processes for carrying this out are described in U.S. Pat. Nos. 6,462,243, 6,465,699, 6,472,572, 6,486,368, and 6,465,696, all of which are herein incorporated by reference.

Another way to convert primary haloalkanes to valuable products is by reaction with nucleophilic materials in the presence of a homogeneous catalyst system. High conversion of primary haloalkanes to useful products is achieved in this reaction and also the selectivity of this reaction to produce the desired products is high. The use of the homogeneous catalyst system increases the reaction rate. This invention is especially advantageous in the case of making alkyl alcohol alkoxylates because it eliminates the expensive step of converting alcohols to alkyl alcohol alkoxylates.

A nucleophilic material is one that will participate in a nucleophilic reaction wherein 1) a bond is broken, i.e., a carbon-halogen bond, 2) the carbon to which the leaving group i.e., a halogen, is attached is an alkyl carbon, and 3) a bond is formed between the carbon and the nucleophilic portion, i.e., the alcohol part of, for example, diethylene glycol, of the nucleophilic material. Preferred nucleophilic materials include those which contain oxygen, nitrogen, and/or sulfur. Dimethylaminopropylamine will react with primary alkyl halides to produce gasoline additives to clean engines. $CH_3SH$ (MeSH) will react with primary alkyl halides to make R—S-Me which is used to control chemical reactions. Other preferred materials include glycols, thioalcohols, and alcohol amines. The most highly preferred nucleophilic materials are polyethylene glycols (PEG), polypropylene glycols, diethylene glycol (DEG), triethylene glycol (TEG), dimethylaminopropylamine, $CH_3SH$, monopropylene glycol (MPG) and monoethylene glycol (MEG). PEG 400 (400 molecular weight) is preferred when the alkyl alcohol alkoxylate is to be used in industrial cleaners. DEG is most preferred for making alkoxylates because of its low cost, its stability under these conditions, its ability to solubilize the catalyst, and because its boiling point helps in the downstream separation steps. DEG is the preferred nucleophilic material when the intended use is in shampoos.

The homogeneous catalyst system comprises at least one metal or metal compound which has the ability to form metal-halogen bonds. Most metals will perform this function. The purpose of the metal and metal compound is to catalyze the coupling reaction and make it go fast enough to make the process practical. Preferably, the metal is selected from metals of Groups VIII, IB and IIB of the periodic table of the elements, CAS version. Particularly preferred catalysts include $FeBr_3$, $CuBr_2$, $CoBr_2$, $MgBr_2$ and $ZnBr_2$. The metals of Groups VIII, IB and IIB of the periodic table of the elements are also described in "Advanced Inorganic Chemistry, Fourth Edition", Authored by F. A. Cotton and G. Wilkinson, A Wiley Interscience Publication, 1980. Zn is most highly preferred because it gives the fastest rates and the highest yields and $Br_2$ is preferred because the metal-Br bond is one of the strongest metal-halogen bonds. Other metal compounds that can be added include metal acetates, carbonates, alkoxylates, nitrates, etc. because they will form metal-halogen bonds.

FIG. 1 illustrates one embodiment of this invention wherein primary haloalkanes are made from alkanes. Alkane and halogen may be introduced into the halogenation reactor 10 through feed lines 12 and 14, respectively. Internal haloalkanes, which may be a mixture of mono-, di-, and tri-, etc. haloalkanes, are produced and are introduced into separator 16, which may be a distillation column, through line 18 along with unreacted alkane. The unreacted alkane is separated and may be recycled to reactor 10 through recycle line 19. The haloalkanes are introduced to separator 20, which may be a distillation column, through line 22. The monohaloalkanes are separated from the di- and tri-, etc. haloalkanes and transferred to catalytic distillation column 24 through line 26. The di-, tri-, etc. haloalkanes may be transferred through line 28 to the hydrogenation unit 30 wherein they may be hydrogenated to monohaloalkanes and recycled to separator 20 through recycle line 32. Hydrogen enters through feed line 29 and any hydrogen halide produced exits through line 31.

The catalytic distillation takes place as described above in column 24 and the light ends 33 leave at the top of the column 24. The desired primary monohaloalkane exits through bottoms line 34 and is introduced into separator 36, which may be a distillation column, wherein the desired primary monohaloalkane is separated and exits through overhead line 38 and the heavy ends 40 leave through the bottom of separator 36.

The primary monohaloalkanes made by the process of this invention can be used in a variety of processes to make a variety of products, including alcohols, olefins, alkyl alcohol alkoxylates, and many others. For example, the primary monohaloalkanes made by the process of this invention may be used in a process comprising direct alkoxylation coupling (DAC) of alkyl halides with a nucleophilic material which is capable of reacting to form alkoxylates in the presence of a homogeneous catalyst system to produce alkyl alcohol alkoxylates, wherein the homogeneous catalyst system comprises at least one metal or metal compound which has the ability to form metal-halogen bonds. This process is described in detail in copending, commonly assigned application entitled "CONVERSION OF ALKYLHALIDES INTO ALCOHOL ALKOXYLATES", filed concurrently herewith, which is herein incorporated by reference in its entirety.

Direct alkoxylation coupling (DAC) is the reaction which allows the direct alkoxylation of haloalkanes to form alkyl alcohol alkoxylates (AAA). The haloalkanes are reacted with a nucleophilic material that is capable of reacting to form an alkoxylates in the presence of a homogeneous catalyst system to produce AAA or a mixture of AAA and olefins, wherein the homogeneous catalyst system comprises at least one metal or metal compound which has the ability to form metal-halogen bonds. The reaction may be carried out at a temperature from 100 to 200° C., preferably 140 to 160° C. In a preferred embodiment, the reactants and the catalyst are dissolved in the nucleophilic material.

A nucleophilic material is one that will participate in a nucleophilic reaction wherein 1) a bond is broken, i.e., a carbon-halogen bond, 2) the carbon to which the leaving group i.e., a halogen, is attached is an alkyl carbon, and 3) a bond is formed between the carbon and the nucleophilic portion, i.e., the alcohol part of, for example, diethylene glycol, of the nucleophilic material. Preferred nucleophilic materials for use in this invention include those which contain oxygen, nitrogen, and/or sulfur, most preferably oxygen. The most highly preferred nucleophilic materials are polyethylene glycols (PEG), polypropylene glycols, diethylene glycol (DEG), triethylene glycol (TEG), monopropylene glycol (MPG) and monoethylene glycol (MEG). PEG 400 (400 molecular weight) is preferred when the AAA is to be used in industrial cleaners. DEG is most preferred because of its low cost, its stability under these conditions, its ability to solubilize the catalyst, and because its boiling point helps in the downstream separation steps. DEG is preferred when the intended use of the AAA is in shampoos.

The homogeneous catalyst system comprises at least one metal or metal compound which has the ability to form metal-halogen bonds. Most metals will perform this function. The purpose of the metal and metal compound is to catalyze the direct alkoxylation coupling reaction and make it go fast enough to make the process practical. Preferably, the metal is selected from metals of Groups VIII, IB and IIB of the periodic table of the elements, CAS version. The metals of Groups VIII, IB and IIB of the periodic table of the elements are also described in "Advanced Inorganic Chemistry, Fourth Edition", Authored by F. A. Cotton and G. Wilkinson, A Wiley Interscience Publication, 1980. Particularly preferred catalysts include $FeBr_3$, $CuBr_2$, $CoBr_2$, $MgBr_2$ and $ZnBr_2$. Zn is most highly preferred because it gives the fastest rates and the highest yields and $Br_2$ is preferred because the metal-Br bond is one of the strongest metal-halogen bonds. Other metal compounds that can be added include metal acetates, carbonates, alkoxylates, nitrates, etc. because they will form metal-halogen bonds.

The alkyl alcohol alkoxylates may be made by introducing an internal haloalkane feed into a catalytic distillation column; isomerizing at least a portion of the internal haloalkane feed in the presence of an internal haloalkane isomerization catalyst at a temperature at or above the boiling point of the internal haloalkanes and below the temperature and pressure at which hydrogen halide is formed to form primary haloalkanes; removing the primary haloalkanes from the catalytic distillation column; and direct alkoxylation coupling of primary haloalkanes with a nucleophilic material that is capable of reacting to produce alkoxylates in the presence of a homogeneous catalyst system to produce alkyl alcohol alkoxylates, wherein the homogeneous catalyst system comprises at least one metal or metal compound which has the ability to form metal-halogen bonds. An internal haloalkane for the above process may be made by halogenating at least one alkane to produce at least one internal haloalkane.

Another embodiment of this invention comprises a method for enhanced oil recovery which comprises (a) making alkyl alcohol alkoxylates as described above; (b) providing the alkyl alcohol alkoxylates to at least a portion of a hydrocarbon containing formation; and (c) allowing the alkyl alcohol alkoxylates to interact with hydrocarbons in the hydrocarbon containing formation.

Hydrocarbons may be recovered from hydrocarbon containing formations by penetrating the formation with one or more wells. Hydrocarbons may flow to the surface through the wells. Conditions (e.g., permeability, hydrocarbon concentration, porosity, temperature, pressure) of the hydrocarbon containing formation may affect the economic viability of hydrocarbon production from the hydrocarbon containing formation. A hydrocarbon containing formation may have natural energy (e.g., gas, water) to aid in mobilizing hydrocarbons to the surface of the hydrocarbon containing formation. Natural energy may be in the form of water. Water may exert pressure to mobilize hydrocarbons to one or more production wells. Gas may be present in the hydrocarbon containing formation at sufficient pressures to mobilize hydrocarbons to one or more production wells. The natural energy source may become depleted over time. Supplemental recovery processes may be used to continue recovery of hydrocarbons from the hydrocarbon containing formation. Examples of supplemental processes include waterflooding, polymer flooding, alkali flooding, thermal processes, solution flooding or combinations thereof.

In an embodiment, hydrocarbons may be produced from a hydrocarbon containing formation by a method that includes treating at least a portion of the hydrocarbon containing formation with a hydrocarbon recovery composition. In certain embodiments, at least a portion of the hydrocarbon containing formation may be oil wet. In some embodiments, at least a portion of the hydrocarbon formation may include low salinity water. In other embodiments, at least a portion of the hydrocarbon containing formation may exhibit an average temperature of less than 50° C. Fluids, substances or combinations thereof may be added to at least a portion of the hydrocarbon containing formation to aid in mobilizing hydrocarbons to one or more production wells in certain embodiments. One example of such a process is described in U.S. Patent Application Publication No. 2004/0177958, which is herein incorporated by reference in its entirety.

Another embodiment comprises a method for making a detergent composition which comprises (a) making alkyl alcohol alkoxylates as described above; and (b) adding to the alkyl alcohol alkoxylates (1) at least one builder, optionally, (2) at least one co-surfactant, and, optionally, (3) other conventional detergent ingredients. Such compositions, conventional ingredients and methods for making them are described in U.S. Patent Application Publication No. 2005/0153869, which is herein incorporated by reference in its entirety.

Suitable silicate builders include water-soluble and hydrous solid types and including those having chain-, layer-, or three-dimensional-structure as well as amorphous-solid silicates or other types, for example especially adapted for use in non-structured-liquid detergents. Also suitable for use herein are synthesized crystalline ion exchange materials or hydrates thereof having chain structure and a composition represented by the following general formula in an anhydride form: $xM_2O.ySiO_2.zM'O$ wherein M is Na and/or K, M' is Ca and/or Mg; y/x is 0.5 to 2.0 and z/x is 0.005 to 1.0 as taught in U.S. Pat. No. 5,427,711, Sakaguchi et al, Jun. 27, 1995, incorporated herein by reference. Aluminosilicate builders, such as zeolites, are especially useful in granular detergents, but can also be incorporated in liquids, pastes or gels.

The detergent compositions according to the present invention preferably further comprise surfactants, herein also referred to as co-surfactants. It is to be understood that surfactants prepared in the manner of the present invention may be used singly in cleaning compositions or in combination with other detersive surfactants. Typically, fully formulated cleaning compositions will contain a mixture of surfactant types in order to obtain broad-scale cleaning performance over a variety of soils and stains and under a variety of usage conditions. A typical listing of anionic, nonionic, cationic, ampholytic and zwitterionic classes, and species of these co-surfactants, is given in U.S. Pat. No. 3,664,961 issued to Norris on May 23, 1972, incorporated herein by reference. Amphoteric surfactants are also described in detail in "Amphoteric Surfactants, Second Edition", E. G. Lomax, Editor (published 1996, by Marcel Dekker, Inc.) McCutcheon's, Emulsifiers and Detergents, Annually published by M. C. Publishing Co., and Surface Active Agents and Detergents" (Vol. I and II by Schwartz, Perry and Berch), all of which are incorporated herein by reference.

Another embodiment comprises a method for making a personal care composition which comprises (a) making alkyl alcohol alkoxylates as described above; and (b) adding to the alkyl alcohol alkoxylates (1) a cosmetically acceptable vehicle and, optionally, (2) at least one sunscreen. Methods for making such compositions are described in U.S. Patent Application Publications Nos. 2005/0048091 and 2005/0196362, which are herein incorporated by reference in their entirety.

The cosmetically-acceptable vehicle is generally present in a safe and effective amount, preferably from 1% to 99.99%, more preferably from about 20% to about 99%, especially from about 60% to about 90%. The cosmetically-acceptable vehicle can contain a variety of components suitable for rendering such compositions cosmetically, aesthetically or otherwise, acceptable or to provide them with additional usage benefits. The components of the cosmetically-acceptable vehicle should be physically and chemically compatible with the branched ester component and should not unduly impair the stability, efficacy or other benefits associated with the personal care compositions of the invention.

Suitable ingredients for inclusion in the cosmetically-acceptable vehicle are well known to those skilled in the art. These include, but are not limited to, emollients, oil absorbents, antimicrobial agents, binders, buffering agents, denaturants, cosmetic astringents, film formers, humectants, surfactants, emulsifiers, sunscreen agents, oils such as vegetable oils, mineral oil and silicone oils, opacifying agents, perfumes, coloring agents, pigments, skin soothing and healing agents, preservatives, propellants, skin penetration enhancers, solvents, suspending agents, emulsifiers, cleansing agents, thickening agents, solubilizing agents, waxes, inorganic sunblocks, sunless tanning agents, antioxidants and/or free radical scavengers, chelating agents, suspending agents, sunless tanning agents, antioxidants and/or radical scavengers, anti-acne agents, anti-dandruff agents, anti-inflammatory agents, exfoliants/desquamation agents, organic hydroxy acids, vitamins, natural extracts, inorganic particulates such as silica and boron nitride, deodorants and antiperspirants.

The one or more sunscreens for use herein may be selected from organic sunscreens, inorganic sunscreens and mixtures thereof. Any inorganic or organic sunscreen suitable for use in a personal care composition may be used herein. The level of sunscreen used depends on the required level of Sun Protection Factor, "SPF". In order to provide a high level of protection from the sun, the SPF of the personal care composition should be at least 15, more preferably at least 20. Suitable inorganic sunscreens for use herein include, but are not necessarily limited to, cerium oxides, chromium oxides, cobalt oxides, iron oxides, titanium dioxide, zinc oxide and zirconium oxide and mixtures thereof. The inorganic sunscreens used herein may or may not be hydrophobically-modified, for example, silicone-treated. In preferred embodiments herein, the inorganic sunscreens are not hydrophobically-modified.

Although FIG. 1 and the examples focus on particular embodiments of the invention, it is understood that the invention is not limited to such embodiments or to the embodiments disclosed, but is capable of numerous rearrangements, modifications, and substitutions of parts and elements without departing from the spirit of the invention.

EXAMPLES

Example 1

Separation of Hexane, Bromohexane and Dibromohexane

A mixture of 5 grams of hexane, 5 grams of 1-Bromohexane and 5 grams of 1,2 dibromo hexane were mixed and placed in a 50 ml round bottom flask. A 200 mm Vigreux distilling column and a short path distillation column were attached to the top of the round bottom flask and heat was applied to the round bottom flask via a heating mantle. When the mixture reached 70° C., the hexane was distilled from the mixture, condensed and collected in the receiving flask. After 5 grams had been collected, no more material was condensing. The round bottom flask was heated to 160° C. and the 1-Bromohexane started to distill. 5 grams of material were collected in the receiving flask. Finally, the material remaining in the round bottom flask was tested by gas chromatography (GC) and was shown to be essentially 1,2-dibromo hexane.

Example 2

Conversion of Dibromohexane to Monobromohexane

To demonstrate the conversion of a dibromohexane to a monobromohexane, 2 grams of 2,3-dibromohexane, 0.1 grams of nickel acetate and 100 mls of cyclohexane was added to a small bolt head autoclave. The autoclave was flushed 3 times with 50 psi of nitrogen and then charged with 55 psi of Hydrogen. The vessel was allowed to sit at 25° C. for two hours to activate the nickel. After two hours, a sample was taken from the autoclave via a dip tube and showed only 2,3-dibromohexane. The autoclave was heated to 180° C. and allowed to react for 60 minutes. A sample was taken and showed that half of the starting material had been converted to a mixture of the 2-bromohexane and 3-bromohexane isomers with only about 1% being converted all the way to hexane.

Example 3

Equilibration of 1-bromooctane to the Other Internal Octane Bromide Isomers

To demonstrate the catalyzed interconversion of 1, 2, 3 and 4 substituted isomers of bromooctane, 1 ml of 1-bromooctane was added to a 10 ml Teflon lined screw top stainless steel autoclave. To this was added 0.032 grams of iron tribromide. The autoclave was sealed, placed in a sand bath and heated to 200° C. After 1 hour, the autoclave was cooled, opened and a small sample was taken and analyzed by GC. The data after 1 hour showed that 10.7% of the 1-bromooctane had isomerized to the 2, 3 and 4 substituted mono bromide isomers of octane. From the data collected after 1 hour, an equilibration time of 20 hours at 200° C. was calculated. The top to the autoclave was screwed back into place and the autoclave was placed in the sand bath at 250° C. To make sure an equilibrium distribution would be reached, the autoclave was left in the sand bath for 24 hours, then cooled to room temperature. Another sample of the material was taken from the autoclave and analyzed by GC. It showed an equilibrium about of 5.6% for 1-bromooctane, with the remaining material being the other isomers. The calculated equilibrium value, based on bond energy's, was 6%.

What is claimed is:

1. A process for making primary haloalkanes by catalytic distillation of internal haloalkanes which comprises:
   a) introducing an internal haloalkane feed into a catalytic distillation column;
   b) isomerizing at least a portion of the internal haloalkane feed in the presence of an internal haloalkane isomerization catalyst at a temperature at or above the boiling point of the internal haloalkanes and below the temperature and pressure at which hydrogen halide is formed to form primary haloalkanes; and
   c) removing the primary haloalkanes from the catalytic distillation column.

2. The process of claim 1 wherein the halogen is bromine.

3. The process of claim 1 wherein the monoalkyl halides are monooctanebromides.

4. The process of claim 1 wherein the temperature ranges from 188° C. to 201° C.

5. The process of claim 1 wherein the isomerization catalyst is zinc bromide.

6. The process of claim 1 wherein the metal in the isomerization catalyst is selected from the group consisting of Groups VIII, IB, and IIB of the periodic table of the elements, CAS version.

7. The process of claim 6 wherein the metal in the isomerization catalyst is zinc.

8. The process of claim 1 wherein the isomerization catalyst is a zeolite.

9. The process of claim 1 wherein the internal haloalkane feed is a mixture of monohaloalkanes and haloalkanes which contain 2 or more halogens and i) the monohaloalkanes are separated from the haloalkanes which contain 2 or more halogens, ii) the haloalkanes which contain 2 or more halogens are hydrogenated to produce primary and/or internal monohaloalkanes, and iii) the primary and/or internal monohaloalkanes from step ii) are recycled to step i).

10. A process for making primary haloalkanes from alkanes which comprises:
    a) halogenating at least one alkane to produce at least one internal haloalkane;
    b) introducing the internal haloalkane into a catalytic distillation column;
    c) isomerizing at least a portion of the internal haloalkane in the presence of an internal haloalkane isomerization catalyst at a temperature at or above the boiling point of the internal haloalkane and below the temperature and pressure at which hydrogen halide is formed to form primary haloalkanes; and
    d) removing the primary haloalkanes from the catalytic distillation column.

11. The process of claim 10 wherein the halogen is bromine.

12. The process of claim 10 wherein the monoalkyl halides are monooctanebromides.

13. The process of claim 10 wherein the temperature ranges from 188° C. to 201° C.

14. The process of claim 10 wherein the isomerization catalyst is zinc bromide.

15. The process of claim 10 wherein the metal in the isomerization catalyst is selected from the group consisting of Groups VIII, IB, and IIB of the periodic table of the elements, CAS version.

16. The process of claim 15 wherein the metal in the isomerization catalyst is zinc.

17. The process of claim 10 wherein the isomerization catalyst is a zeolite.

18. The process of claims 10 wherein the internal haloalkane feed is a mixture of monohaloalkanes and haloalkanes which contain 2 or more halogens and i) the monohaloalkanes are separated from the haloalkanes which contain 2 or more halogens, ii) the haloalkanes which contain 2 or more halogens are hydrogenated to produce primary and/or internal monohaloalkanes, and iii) the primary and/or internal monohaloalkanes from step ii) are recycled to step i).

* * * * *